US011717277B2

(12) United States Patent
Horeman et al.

(10) Patent No.: US 11,717,277 B2
(45) Date of Patent: Aug. 8, 2023

(54) DEVICE FOR TREATMENT OF ANAL FISTULA

(71) Applicant: Super Seton B.V., Amsterdam (NL)

(72) Inventors: Tim Horeman, Leiden (NL); Willem Nerkens, The Hague (NL)

(73) Assignee: SUPER SETON B.V., Amsterdam (NL)

(*) Notice: Subject to any disclaimer, the term of this patent is extended or adjusted under 35 U.S.C. 154(b) by 208 days.

(21) Appl. No.: 16/345,324

(22) PCT Filed: Oct. 26, 2017

(86) PCT No.: PCT/EP2017/077524
§ 371 (c)(1),
(2) Date: Apr. 26, 2019

(87) PCT Pub. No.: WO2018/078058
PCT Pub. Date: May 3, 2018

(65) Prior Publication Data
US 2019/0269389 A1  Sep. 5, 2019

(30) Foreign Application Priority Data
Oct. 26, 2016 (GB) ...................................... 1618129

(51) Int. Cl.
*A61B 17/00* (2006.01)
*A61B 17/064* (2006.01)
(Continued)

(52) U.S. Cl.
CPC ...... *A61B 17/0057* (2013.01); *A61B 17/0643* (2013.01); *A61B 17/0487* (2013.01);
(Continued)

(58) Field of Classification Search
CPC ............ A61B 17/0487; A61B 17/0643; A61B 2017/00641; A61B 2017/00646;
(Continued)

(56) References Cited

U.S. PATENT DOCUMENTS 5,902,319 A * 5/1999 Daley ................ A61B 17/0487
606/219
2008/0051831 A1* 2/2008 Deal ................ A61B 17/12099
606/213
(Continued)

FOREIGN PATENT DOCUMENTS

CN       103536319 B     5/2016
EP         2926740 A1   10/2015
(Continued)

OTHER PUBLICATIONS

Evans, Rachel; UKIPO Combined Search and Examination Report, dated Mar. 15, 2017, 1-9.
(Continued)

*Primary Examiner* — Darwin P Erezo
*Assistant Examiner* — Brigid K Byrd

(57) ABSTRACT

Disclosed is a device (100) for treatment of anal fistula. The device comprises a hollow wire (110) comprising a first end (112) and a second end (114) opposite to the first end, the hollow wire is operable to be received by a fistula track with both first and second ends projecting out of the fistula track. The device also comprises an insert (120) operable to be partially inserted into the first end of the hollow wire and to project out of the first end. The device further comprises an applicator (130) operable to be removably arranged on the second end of the hollow wire when the hollow wire is placed in the fistula track. The applicator is operable to be held for enabling the projected out insert to be inserted into second end for detachably coupling the first and second ends to form a closed loop around the fistula track.

19 Claims, 3 Drawing Sheets

(51) Int. Cl.
 *A61B 17/04* (2006.01)
 *A61B 17/06* (2006.01)
(52) U.S. Cl.
 CPC ............... *A61B 2017/00641* (2013.01); *A61B 2017/00646* (2013.01); *A61B 2017/00668* (2013.01); *A61B 2017/00893* (2013.01); *A61B 2017/06185* (2013.01)
(58) Field of Classification Search
 CPC ................................ A61B 2017/00668; A61B 17/06166–2017/0619; A61B 2017/00663–00668; A61B 17/10; A61B 17/128; A61B 2017/0488
 See application file for complete search history.

(56) References Cited

U.S. PATENT DOCUMENTS

| | | | | |
|---|---|---|---|---|
| 2011/0046620 A1* | 2/2011 | Lewandowski | ........ | A61B 17/30 606/41 |
| 2011/0071548 A1* | 3/2011 | Yeh | ................. | A61B 17/06166 606/144 |
| 2011/0282373 A1* | 11/2011 | Chekan | ............ | A61B 17/32002 606/170 |
| 2014/0128888 A1* | 5/2014 | McClellan | ....... | A61B 17/06166 606/144 |
| 2014/0227337 A1* | 8/2014 | Keighley | ........... | A61B 17/0057 424/426 |
| 2015/0250460 A1* | 9/2015 | Horeman | ........... | A61B 17/0487 606/228 |
| 2017/0224329 A1* | 8/2017 | Ono | .................... | A61B 17/0487 |
| 2018/0221022 A1* | 8/2018 | Choe | ................ | A61B 17/06166 |

FOREIGN PATENT DOCUMENTS

| | | |
|---|---|---|
| GB | 2489229 A | 9/2012 |
| JP | 2005106092 A | 4/2005 |
| JP | 2005160821 A | 6/2005 |
| WO | 2008024920 A1 | 2/2008 |
| WO | 2011/0151659 A2 | 12/2011 |
| WO | 2012174469 A2 | 12/2012 |
| WO | 2014032813 A1 | 3/2014 |
| WO | 2014164955 A2 | 10/2014 |

OTHER PUBLICATIONS

Mathis, Martin; Written Opinion of the International Searching Authority, daetd May 1, 2018, pp. 1-10.
First Examination Report issued in IN Application No. IN201947019882 dated Sep. 23, 2021, 7 pages.
First Examination Report issued in CN Application No. CN2017800665172 dated Nov. 3, 2021, 17 pages.
First Examination Report issued in JP Application No. 2019-522561 dated Aug. 20, 2021, 20 pages.

* cited by examiner

DEVICE FOR TREATMENT OF ANAL FISTULA

TECHNICAL FIELD

The present disclosure relates generally to a medical device; and more specifically, to a device for the treatment of anal fistula.

BACKGROUND

Many people suffer from Crohn's disease, such as anal fistula. An anal fistula is a tunnel that forms under the peri-anal skin and connects clogged infected glands to an abscess. Typically, the treatment of anal fistula includes abscess drainage through a surgical opening made in the peri-anal skin. Generally, under most circumstances, the fistula track tends to persist after the drainage. Moreover, even if the skin of the surgical opening heals, the persisting fistula track may cause recurrence of an abscess.

Typically, to allow proper healing of the skin of the surgical opening and the fistula track, a seton ring is placed in the fistula track to keep the surgical opening and the fistula track open. Conventionally, the seton ring may be a thread operable to be placed in the fistula track, and thereafter the seton ring may be sutured or knotted outside (over the peri-anal skin). Generally, such outside knot causes pain and discomfort to the patient, and may tend to open with time. Also, the procedure of placing such seton ring is a time consuming and cumbersome process. For example, the seton ring requires precise use of fingers to form loop and knot for the seton ring over the peri-anal skin. Further, precise use of fingers may be required to measure a tightness of such seton ring. Alternatively, a smooth and flexible seton ring may be used for the healing of the fistula track. Specifically, such seton ring uses a connector to join two ends of the seton ring (instead of using knots). However, due to the flexible nature of such seton ring, a procedure of placing such seton ring in the fistula track, particularly, connecting the two ends of the seton ring still remain cumbersome and time consuming.

Therefore, in light of the foregoing discussion, there exists a need to overcome the aforementioned drawbacks associated with treatment for anal fistula.

SUMMARY

The present disclosure seeks to provide a device for treatment of anal fistula. The present disclosure seeks to provide a solution to the existing problem of cumbersome and time consuming process of placing a seton ring in a fistula track. An aim of the present disclosure is to provide a solution that overcomes at least partially the problems encountered in prior art, and assists in easy and efficient placement of a seton ring in a fistula track.

In one aspect, an embodiment of the present disclosure provides a device for treatment of anal fistula, the device comprising: —a hollow wire comprising a first end and a second end opposite to the first end, the hollow wire is operable to be received by a fistula track with both first and second ends projecting out of the fistula track;

an insert operable to be partially inserted into the first end of the hollow wire and to project out of the first end; and an applicator operable to be removably arranged on the second end of the hollow wire when the hollow wire is placed in the fistula track;

wherein the applicator is operable to be held for enabling the projected out insert to be inserted into the second end for detachably coupling the first and second ends to form a closed loop around the fistula track.

Embodiments of the present disclosure substantially eliminate or at least partially address the aforementioned problems in the prior art, and provide a device for treatment of anal fistula with an easy installation technique.

The applicator may comprise a holding portion operable to be held which may be planar. The applicator may comprise an elongate tab. The elongate tab may be coupled to an edge of the planar portion, when present. The applicator may comprise a channel that is operable to removably receive the second end of the hollow wire therein. The elongate tab may comprise the channel which then may run along a length of the elongate tab.

At least a portion of the applicator may be openable so that the channel is openable, e.g. at least a portion of the applicator being formed as an openable gripper such as or a tweezer or plier, for easy removing the applicator from the hollow wire, in particular from the closed loop. The openable portion may be connected to a resilient portion urging the openable portion to an open state. The openable portion of an applicator with an openable portion may be formed to press on the hollow wire when the openable portion is held closed, e.g. by being firmly held with two fingers.

The channel may comprise a narrow section and a broad section extending from the narrow section, such that applicator is operable to be removably arranged on the second end of the hollow wire, in particular when the hollow wire is placed in the fistula track, with the second end of the hollow wire being snugly received by the narrow section and freely received by the broad section.

The openable portion of an applicator with an openable portion may be formed to press on the hollow wire in the narrow section when the openable portion is held closed. The broad section may be operable to receive the second end and to enable the projected out insert to be inserted into the second end and the second end to expand sideways within the broad section. The broad section may support the second end to stabilize the second end and/or to prevent buckling of the second end during the sideways expansion with the insertion of the projected out insert.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
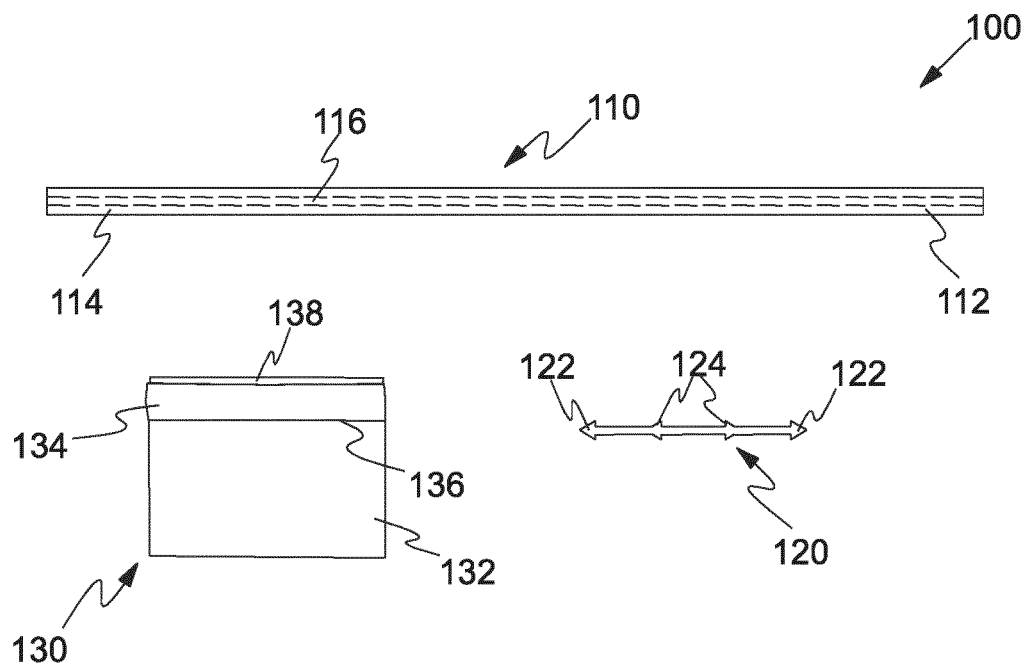
FIG. 1 is a schematic illustration of a device for treatment of anal fistula, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a device for treatment of anal fistula, the device comprising:
- a hollow wire comprising a first end and a second end opposite to the first end, the hollow wire is operable to be received by a fistula track with both first and second ends projecting out of the fistula track;
- an insert operable to be partially inserted into the first end of the hollow wire and to project out of the first end; and
- an applicator operable to be removably arranged on the second end of the hollow wire when the hollow wire is placed in the fistula track;

wherein the applicator is operable to be held for enabling the projected out insert to be inserted into the second end for detachably coupling the first and second ends to form a closed loop around the fistula track.

According to an embodiment of the present disclosure, the device for the treatment of anal fistula, such as cryptoglandular fistula, may be operable to be placed along a length of a fistula track. The device may form a closed loop, with a minimum cross section, around the fistula track. Further, the device may enable in keeping the fistula track open, thereby preventing formation of peri-anal abscesses. Also, the open fistula track may prevent formation of a healed skin over a surgical opening. Furthermore, the device may be loosely arranged in the fistula track to allow drainage of pus from the abscess. The device may enable in curing the fistula by tightening the device around the fistula track. For example, the device may be tightened gradually with time to cut through the anal fistula.

The device comprises a hollow wire comprising a first end and a second end opposite to the first end. The hollow wire may include an opening running along a length of the hollow wire from the first end and the second end. Alternatively, the hollow wire may be at least partially solid, i.e. openings may be formed only at the first and second ends instead of entire length of the hollow wire.

In one embodiment, the hollow wire may include a circular cross-section, i.e. the hollow wire may be a tubular structure.

Alternatively, the hollow wire may have other cross-sections, such as oval or polygonal cross-sections.

In an embodiment, the hollow wire may have an outer diameter of in a range of 1 millimeter (mm) to 3 mm, for example the outer diameter of the hollow wire may be 1.2 mm, 1.5 mm, 2.2 mm, 2.5 mm and so forth. Otherwise, the outer diameter of the hollow wire may be less than 1 mm. Further, the hollow wire may have an inner diameter in a range of 0.35 mm to 2.5 mm, for example the inner diameter of the hollow wire may be 0.50 mm, 1 mm, 1.5 mm, 2 mm and so forth. Alternatively, the inner diameter of the hollow wire may be less than 0.35 mm.

In an embodiment, the hollow wire may be made of silicone or polyurethane. Further, the hollow wire may be soft in construction and highly flexible in nature for conforming to a shape of the fistula track. In one embodiment, the hollow wire may have softness in a range of shore 30-60. For example, the softness of the hollow wire may be shore 35, 40, 45, 50, 55 and so forth. Alternatively, the softness of the hollow wire may be lesser than shore 30.

The hollow wire is operable to be received by the fistula track with both first and second ends projecting out of the fistula track. According to an embodiment, the hollow wire may include a length that suitably covers or closes a fistula track. For example, the length of the hollow wire exceeds a length of the fistula track.

In one embodiment, the hollow wire may further comprise a plurality of lateral holes for containing and releasing medication from therein. The lateral holes may be formed on an outer surface of the hollow wire, and may or may not be formed along the entire length of the hollow wire. Optionally, the lateral holes may have various sizes and shapes. Alternatively, the hollow wire may include a plurality of recesses formed on the outer surface of the hollow wire for containing medication therein. The medication may enable in accelerating a process of healing of the fistula.

The device also comprises an insert operable to be partially inserted into the first end of the hollow wire and to project out of the first end. The insert may be operable to detachably couple the first end and second end of the hollow wire. The insert may comprise an elongated body with sharp ends. For example, the insert may include conical arrow heads at the ends of the insert.

In one embodiment, the insert may comprise sharp ends and a plurality of protrusions along a length of the insert. In an example, the insert may include two protrusions along the length of the insert. Further, the protrusions may have various shapes and sizes, for example, the protrusions may be sharp edges like arrow heads. In one embodiment, the plurality of protrusions may act as a locking mechanism for coupling the first end and second end of the hollow wire. Specifically, the protrusions may be operable to smoothly slide into the first and second ends of the hollow wire, and sharp edges thereof may enable in retaining the insert therein.

In one embodiment, an outer diameter of the insert (i.e. elongated body thereof) may be smaller than the inner diameter of the hollow wire. However, the sharp ends and the protrusions of the insert may include a larger outer diameter (or length) compared to the inner diameter of the hollow wire. Accordingly, the sharp ends and the protrusions may smoothly slide into the first and second ends of the hollow wire but the sharp edges thereof may enable in retaining the insert in the first and second ends.

According to an embodiment, the insert may be made of a material selected from a group consisting of polyurethane, polypropylene, thermoplastic and any combination thereof.

The device also comprises an applicator operable to be removably arranged on the second end of the hollow wire when the hollow wire is placed in the fistula track. The applicator is operable to be held for enabling the projected out insert to be inserted into second end for detachably coupling the first and second ends to form a close loop around the fistula track.

In one embodiment, the applicator may be made of a material selected from a group consisting of plastic, fiber-reinforced plastic, thermoplastic and any combination thereof. The material may be resilient.

In one embodiment, the applicator may include a planar portion operable to be held. The planar portion may be configured to have various sizes and shapes, such as a rectangle or a hexagon or a polygon. In an example, the planar portion may include a rectangular shape. The planar portion of the applicator may provide area to be held between two fingers (i.e. by pinching) for firmly holding the applicator.

According to an embodiment, the applicator may also include an elongate tab. The elongate tab may be coupled to an edge of the planar portion, when present. In an embodiment, the elongated tab may be a tubular structure operable to be removably arranged on the second end of the hollow wire. Further, when coupled to an edge of the planar portion, the length of the elongate tab may be equal to the length of the planar portion.

In one embodiment, the elongate tab may include a channel, which may run along a length (i.e. longitudinal length) of the elongate tab. The channel is operable to removably receive the second end of the hollow wire therein. Specifically, the second end may be snugly received by the channel of the elongate tab, when the second end of the hollow wire is pressed against the channel of the elongate tab.

In one embodiment, the channel may include two sections such as a narrow section and a broad section extending from the narrow section of the channel. Further, the second end of the hollow wire may be snugly received by the narrow section and freely received by the broad section. According to an embodiment, a diameter of the channel in the narrow section may be smaller than a diameter of the channel at the broad section. Further, the diameter of the second end of the hollow wire may be larger as compared to the diameter of the narrow section of the channel, and may be smaller as compared to the diameter of the broad section of the channel. Therefore, the channel may receive the second end of the hollow wire snugly (i.e. presses the hollow wire slightly) in the narrow section, and freely (i.e. without being pressed) at the broad section.

In one embodiment, the applicator is operable to be held for enabling the projected out insert to be inserted into the second end for coupling the first and second ends to form the closed loop around the fistula track. Specifically, when the hollow wire is received in the fistula track, the applicator (arranged on the second end of the hollow wire) may be firmly held, e.g. firmly held with two fingers, to easily insert the projected out insert (carried by the first end of the hollow wire) into to the second end to from closed loop. Therefore, the applicator arranged on the second end of the hollow wire stabilizes the second end while inserting the projected out insert (of the first end) into the second end.

According to an embodiment, the second end of the hollow wire in the broad section is operable to receive the projected out insert (particularly, a sharp end and a protrusion of the insert) to allow the second end to expand sideways. Further, the broad section supports the second end to prevent buckling of the second end during the sideways expansion with the insertion of the projected out insert.

In exemplary use, a surgical insertion may be made in the peri-anal skin involving an anal fistula for inserting the hollow wire of the device into the fistula track. In an example, a guide wire may be coupled to the second end of the hollow wire for slidably inserting the hollow wire through the fistula track. The guide wire (along with the second end of the hollow wire) may pass through the fistula track and project out of an anal canal. Further, a surgical instrument (such as forceps) may be used to extract (pull out) the second end of the hollow wire by pulling the guide wire. Thereafter, the guide wire may be removed from the second end, and the applicator may be removably arranged on the second end of the hollow wire. The first end of the hollow wire may be partially receiving the insert therein. In such instance, the applicator (particularly, the planar portion) may enable in firmly holding the second end of the hollow wire for longitudinally inserting the projected out insert from the first end into the second end to form the closed loop. Once the first and second ends of the hollow wire are coupled with the insert (i.e. the sharp ends and the protrusion of the insert received by the first and second ends), the applicator may be removed from the second end of the hollow wire.

According to an embodiment of the present disclosure, an average time of 1 minute may be required to couple the first and second ends of the hollow wire (using the applicator) to from the closed loop. Further, the applicator enables in conveniently managing the first and second ends of the hollow wire while coupling. Therefore, the device of the present disclosure makes the process of impaling the hollow wire in the fistula track, less cumbersome and fast.

In one embodiment, a connection resisting pulling force of up to 5 Newton (N) may be required (sideways) on the closed loop to dismantle or open the closed loop. Further, the closed loop formed within 1 minute and having a connection resisting pulling force of up to 5N may not exhibit connection failure for at least 2 weeks.

The present disclosure provides a device for an efficient treatment of anal fistula. The present device forms a closed loop around a fistula track using a hollow wire, an applicator and an insert. The applicator may provide an easy and convenient means (connection) for connecting two ends of a hollow wire which passes through the fistula track. In an example, the first and second ends of the hollow wire may be coupled in less than 1 minute to from the close loop. Further, the closed loop formed is non obstructive to contours of skin around the body part involving the anal fistula.

DETAILED DESCRIPTION OF THE DRAWINGS

Referring to FIG. 1, illustrated is a schematic illustration of a device 100 for treatment of anal fistula, in accordance with an embodiment of the present disclosure. The device 100 includes a hollow wire 110, an insert 120 and an applicator 130. The hollow wire 110 includes a first end 112 and a second end 114 opposite to the first end 112. The hollow wire 110 also includes an opening 116 running along a length from the first end 112 and the second end 114. The insert 120 includes sharp ends 122 and a plurality of protrusions 124 along a length of the insert 120. The applicator 130 includes a planar portion 132 and an elongate tab 134 coupled to an edge 136 of the planar portion 132. Here, the planar portion 132 and the elongate tab 134 have equal length. The elongate tab 134 comprises a channel 138 running along a length of the elongate tab 134.

Figure 2:
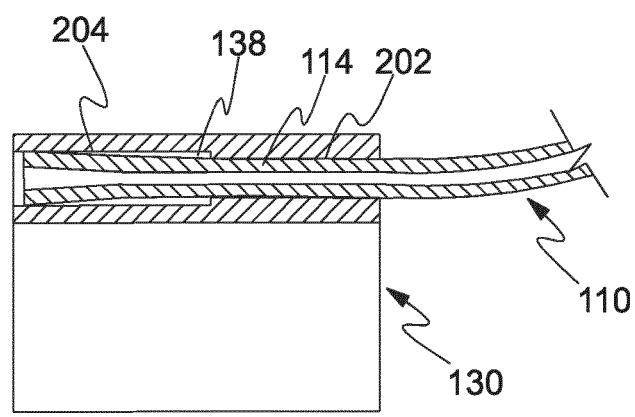
FIG. 2 is a cross-sectional view of an applicator of the device of FIG. 1 removably arranged on a second end of a hollow wire, in accordance with an embodiment of the present disclosure.

FIG. 2 is a cross-sectional view of the applicator 130 (of the device 100 of FIG. 1) removably arranged on the second end 114 of the hollow wire 110, in accordance with an embodiment of the present disclosure. As shown, the second end 114 of the hollow wire 110 is received in the channel 138. The channel 138 includes a narrow section 202 and a broad section 204 extending from the narrow section 202. Further, the second end 114 of the hollow wire 110 is snugly received by the narrow section 202 and freely received by the broad section 204.

Figure 3:
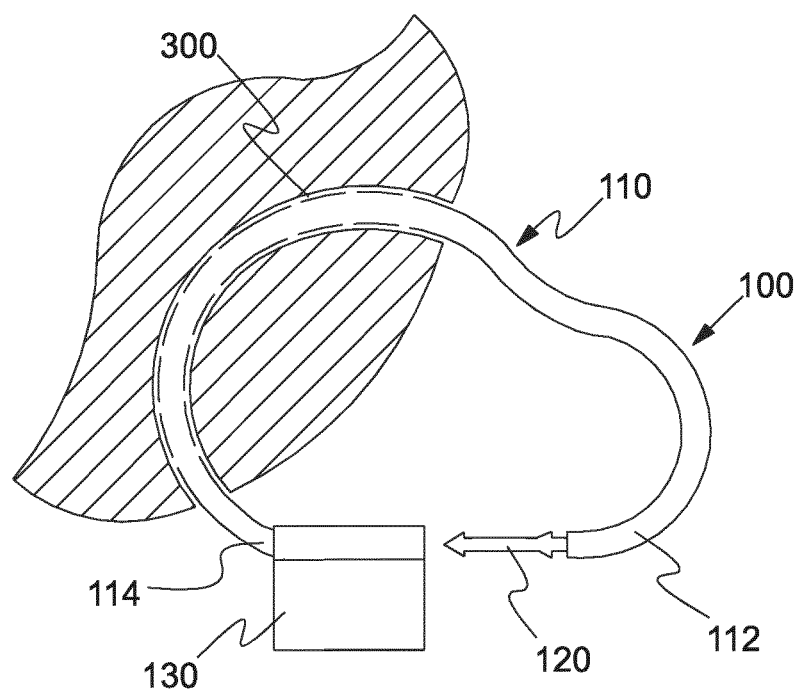
FIG. 3 is a schematic illustration of the device of FIG. 1 in an implanting state, in accordance with an embodiment of the present disclosure.

Referring now to FIG. 3, illustrated is a schematic illustration of the device 100 of FIG. 1 in an implanting state, in accordance with an embodiment of the present disclosure. As shown, the hollow wire 110 is surgically implanted in a fistula track 300 with both the first and second ends 112, 114 projecting out of the fistula track 300. The insert 120 is partially inserted into the first end 112 of the hollow wire 110 and projects out of the first end 112. The applicator 130 is removably arranged on the second end 114 of the hollow wire 110. Therefore, the applicator 130 is operable to be held for enabling the projected out insert 120 to be inserted into second end 114, for detachably coupling the first and second ends 112, 114 to form a closed loop around the fistula track 300.

Figure 4:
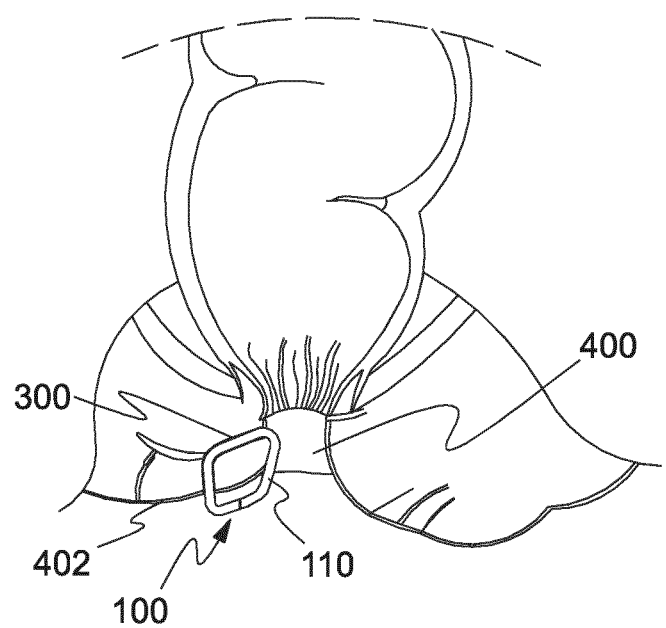
FIG. 4 is a schematic illustration of the device of FIG. 1 in a used state, in accordance with an embodiment of the present disclosure.

FIG. 4 is a schematic illustration of the device 100 of FIG. 1 in a used state, in accordance with an embodiment of the present disclosure. As shown, the hollow wire 110 is implanted in the fistula track 300 forming a closed loop around an anal canal 400. Further, the applicator 130 (shown in FIGS. 1-3) is shown removed from the hollow wire 110. Therefore, the closed loop formed by the hollow wire 110 is non obstructive to the contours of peri-anal skin 402.

Figure 5:
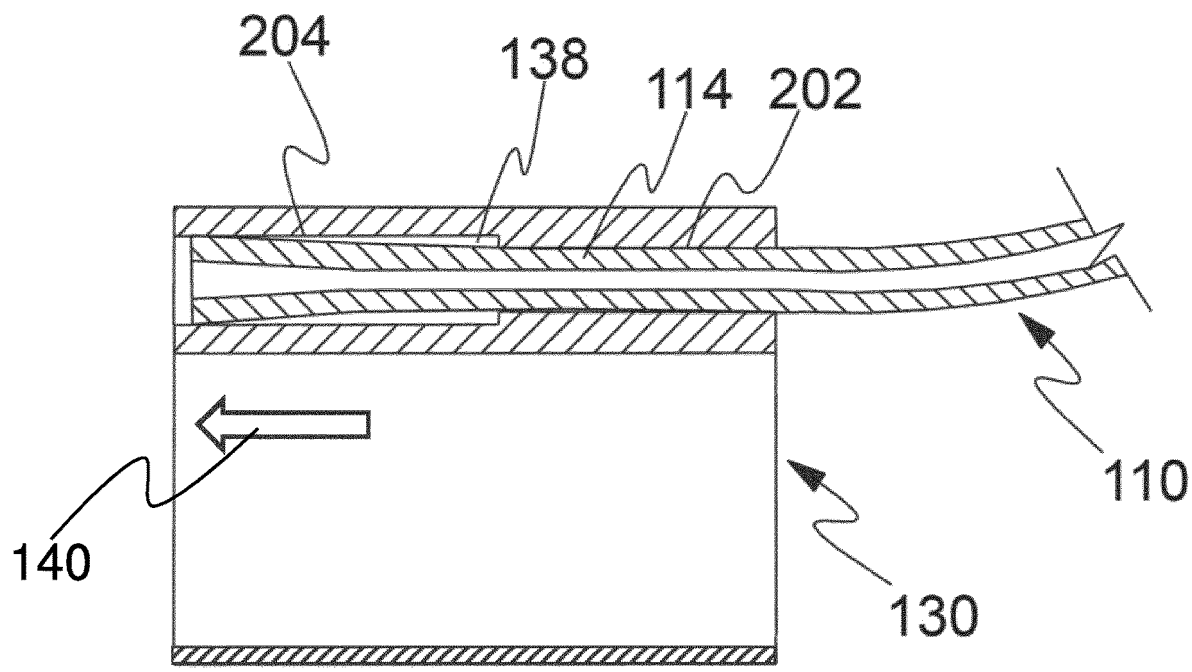
FIG. 5 and FIG. 6 are cross-sectional views of an applicator of the device according to FIG. 1 removably arranged on a second end of a hollow wire, in accordance with an embodiment of the present disclosure.
Figure 6:
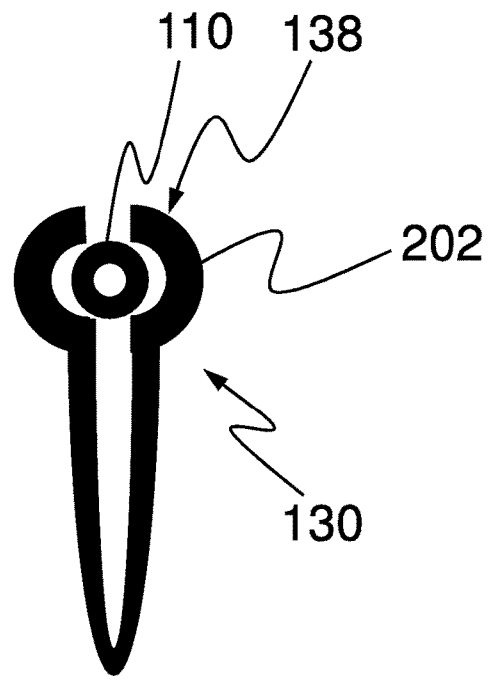

FIG. 5 is a cross-sectional view of an applicator 130 removably arranged on the second end 114 of the hollow wire 110, in accordance with an embodiment of the present disclosure. FIG. 6 is a perpendicular cross sectional view of the applicator of FIG. 5. The channel 138 includes a narrow section 202 and a broad section 204 extending from the narrow section 202. The applicator 130 is formed as an openable gripper, here in the form of a resilient tweezer urged to an open state, so that the channel 138 is openable for easy arranging the applicator 130 on the hollow wire 110 and/or for easy removing the applicator 130 from the closed loop. FIG. 5 shows the second end 114 of the hollow wire 110 received in the channel 138. The applicator 130 provides area to be held between two fingers (i.e. by pinching) for firmly holding the applicator 130 closed and pressing the channel 138 onto the wire 110 so that he second end 114 of the hollow wire 110 is snugly received by the narrow section 202 and freely received by the broad section 204. Further, the shown applicator 130 is provided with an optional mark 140 indicating a use orientation, e.g. indicating the narrow section 202 or the broad section 204.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A device for treatment of anal fistula, the device comprising:

a hollow wire comprising a first end and a second end opposite to the first end having a second end outer diameter, the hollow wire is operable to be received by a fistula track with both the first and second ends projecting out of the fistula track;

an insert operable to be partially inserted into the first end of the hollow wire and to project out of the first end; and an applicator operable to be removably arranged on the second end of the hollow wire when the hollow wire is placed in the fistula track;

wherein the applicator is operable to be held for enabling the projected out insert to be inserted into the second end for detachably coupling the first and second ends to form a closed loop around the fistula track;

wherein at least a portion of the applicator is openable, and wherein the applicator comprises a channel that is operable to removably receive the second end of the hollow wire therein, the channel further forming, when the openable portion is held closed:

a narrow section having a narrow section inner diameter less than the second end outer diameter; and a broad section extending from the narrow section and having a broad section inner diameter greater than the second end diameter;

such that when the openable portion is held closed on the second end of the hollow wire, the second end of the hollow wire is snugly received by the narrow section and freely received by the broad section for enabling insertion of the projected out insert through the broad section and into the second end while the openable portion is held closed on the second end of the hollow wire.

2. The device according to claim 1, wherein the applicator comprises a planar portion operable to be held, and an elongate tab coupled to an edge of the planar portion, the elongate tab comprises the channel running along a length of the elongate tab.

3. The device according to claim 1, wherein the second end in the broad section allows the second end to expand sideways within the broad section when the openable portion is held closed on the second end and the projected out insert is being inserted into the second end.

4. The device according to claim 3, wherein the broad section supports the second end to prevent buckling of the second end during the sideways expansion with the insertion of the projected out insert.

5. The device according to claim 1, wherein the insert comprises sharp ends and a plurality of protrusions along a length of the insert.

6. The device according to claim 1, wherein at least one of:

the hollow wire is made of silicone or polyurethane;
the hollow wire further comprises a plurality of lateral holes for containing and releasing medication from therein;
the insert is made of a material selected from a group consisting of polyurethane, thermoplastic and any combination thereof; and
the applicator is made of a material selected from a group consisting of plastic, fiber-reinforced plastic, thermoplastic and any combination.

7. The device according to claim 1, wherein the insert comprises arrowheads along a length of the insert.

8. The device according to claim 1, wherein an outer diameter of the insert is smaller than an inner diameter of the hollow wire.

9. The device according to claim 1, further comprising a guide wire coupled to the second end of the hollow wire.

10. The device according to claim 1, wherein the openable portion of the applicator is connected to a resilient portion urging the openable portion to an open state.

11. The device according to claim 1, wherein the openable portion of the applicator is formed to press on the second end of the hollow wire when the openable portion is held closed.

12. The device according to claim 1, wherein the applicator is provided with a mark indicating a use orientation.

13. A device for treatment of anal fistula, the device comprising:
a hollow wire comprising a first end and a second end opposite to the first end, the hollow wire is operable to be received by a fistula track with both the first and second ends projecting out of the fistula track, the second end having a second end outer diameter;
an insert operable to be partially inserted into the first end of the hollow wire and to project out of the first end; and
an applicator operable to be removably arranged on the second end of the hollow wire when the hollow wire is placed in the fistula track and comprising:
a planar portion operable to be held;
an elongate tab coupled to an edge of the planar portion, the elongate tab comprises a channel running along a length of the elongate tab, wherein the channel is operable to removably receive the second end of the hollow wire therein; and
wherein the channel comprises:
a narrow section having a narrow section inner diameter that is less than the second end outer diameter; and
a broad section extending from the narrow section and having a broad section inner diameter that is greater than the second end outer diameter;
such that when an openable portion of the applicator is held closed on the second end of the hollow wire the second end of the hollow wire is snugly received by the narrow section and freely received by the broad section; and
the applicator enables, while the openable portion of the applicator is held closed on the second end of the hollow wire, insertion of the projected out insert to bo through the broad section and into the second end for detachably coupling the first and second ends to form a closed loop around the fistula track.

14. The device according to claim 13, wherein the second end in the broad section is operable to receive the projected out insert to allow the second end to expand sideways within the broad section when the openable portion is held closed.

15. The device according to claim 14, wherein the broad section supports the second end to prevent buckling of the second end during the sideways expansion with the insertion of the projected out insert.

16. The device according to claim 13, wherein the insert comprises sharp ends and a plurality of protrusions along a length of the insert.

17. The device according to claim 13, wherein at least one of:
the hollow wire is made of silicone or polyurethane;
the hollow wire further comprises a plurality of lateral holes for containing and releasing medication from therein;
the insert is made of a material selected from a group consisting of polyurethane, thermoplastic and any combination thereof; and
the applicator is made of a material selected from a group consisting of plastic, fiber-reinforced plastic, thermoplastic and any combination thereof.

18. The device according to claim 13, wherein the openable portion of the applicator is configured to function as an openable gripper.

19. A method of implanting a seton, comprising:
providing a hollow wire comprising a first end and a second end opposite the first end and having a second end outer diameter;
implanting the wire in a fistula track with both the first and second ends projecting out of the fistula track;
partially inserting an insert into the first end of the hollow wire and to project out of the first end;
providing an applicator of which at least a portion is openable, and comprising a channel that is operable to removably receive the second end of the hollow wire therein, the channel further forming, when the openable portion is held closed:
a narrow section having a narrow section inner diameter that is smaller than the second end outer diameter; and
a broad section extending from the narrow section and having a broad section inner diameter that is larger than the second end outer diameter;
removably arranging the applicator on the second end of the hollow wire when the hollow wire is placed in the fistula track; and
with the openable portion held closed on the second end of the hollow wire, snugly receiving the second end of the hollow wire by the narrow section, freely receiving the second end of the hollow wire by the broad section and inserting the projected out insert into the second end.

* * * * *